United States Patent Office

Plant Pat. 2,713
Patented Feb. 14, 1967

2,713
PLUM TREE

Charles L. Vinyard, Fresno, Calif., assignor to Hervin Farms, Inc., Fresno, Calif., a California organization Filed Oct. 19, 1965, Ser. No. 498,173
1 Claim. (Cl. Pit.—38)

The present invention relates to a plum tree and more particularly to a new and distinct variety thereof which is broadly characterized by vigorous, profuse and regular bearing; early bloom, and the production of unusually large, early maturing, finely fleshed plums which are evenly distributed along the branches of the tree.

The instant variety plum tree blooms somewhat earlier than the Beauty plum tree (unpatented) and its fruit ripens three to four days earlier than the Beauty, which the instant variety most closely resembles. Its fruit distinguishes, however, from the Beauty in its larger size, more deeply set stem cavity, and its firmer flesh which has greater resistance to bruising. The plum tree of the instant variety is further distinguished from the Beauty plum tree in that while being a profuse bearer, the fruit does not set in clusters, as does the fruit of the Beauty, but rather is more evenly distributed along the branches for easier and more selective thinning.

The present variety of plum tree was discovered by me as a sport growing on a Beauty plum tree (unpatented) at Hervin Farms, Inc., in April 1960, Fresno, County of Fresno, California. The instant variety was asexually reproduced by budding scions, from the sport to a seedling plum tree in 1961. Scions from this tree were June budded in 1962 to thirty Lovell peach tree rootstocks (unpatented) in a test plot at Burchell Nursery, Modesto, Stanislaus County, California. The trees fruited in June 1964 and the fruit and tree characteristics resulting from such budding proved identical to those of the original tree.

The accompanying drawing is a dye transfer color print of a photograph showing the leaves and several mature fruit of the subject variety with one of the fruit divided on its suture plane to reveal flesh coloration and pit characteristics.

Referring more specifically to the pomological details of this new and distinct variety of plum tree, the following has been observed under the ecological conditions prevailing at the test plot at Modesto, Stanislaus County, California, and is an outlined description thereof. All major color plate identifications are by reference to the Nickerson Color Fan of the American Horticultural Council.

*Tree*

Size: Medium to large, sturdy, vigorous, spreading with density determined by pruning methods; more spreading than the Santa Rosa plum tree (unpatented); generally about the same as the Beauty plum tree (unpatented).

Trunk: Large, generally smooth, similar to the Beauty plum tree.
- *Size.*—Medium to stocky.
- *Surface character.*—Generally smooth.
- *Color.*—Dark olive brown, similar to the Beauty plum tree.

Branches: Lenticels, average number, medium sized.

Leaves:
- *Size.*—Medium to large.
- *Length.*—Average 120 millimeters.
- *Width.*—Average 45 millimeters.

- *Shape.*—Slender, oblong, acuminate and tapered at the petiole.
- *Color.*—Upper surface, Dark Green (5G 3/4); underside, moderate Olive Green (7.5GY 4/4).
- *Marginal form.*—Medium fine, serrated.
- *Glands.*—Globose, usually two in opposed relation on base of leaves, some on petiole, light green.
- *Petiole.*—Medium long, medium slender.
- *Stipules.*—Usually two.

Flowers: Generally early, medium to large, white, somewhat earlier than the Beauty plum tree.

*Fruit*

Maturity three to four days earlier than the Beauty plum tree.

Size: Generally large, larger than the Beauty plum tree, averaging 4 x 5 size class. Diameter—transverse in suture plane, average 45 millimeters; diameter—transverse at right angles to suture plane, average 53 millimeters.

Form: Generally globose, symmetrical, slightly flattened at base and apex, however, not as much as the fruit from the Elderado plum tree, has slight suture somewhat darker than the skin.
- *Lips.*—Generally equal, not pronounced.
- *Ventral surface.*—Somewhat flattened.
- *Cavity.*—Conical.
- *Base.*—Somewhat oval.
- *Apex.*—Somewhat flattened to slightly rounded, pistil point somewhat indented at apex.
- *Stem.*—Length, average 18.5 millimeters.
- *Diameter.*—Average 2.15 millimeters.

Skin: Medium tough, tenacious to flesh, loosening when full ripe.
- *Texture.*—Smooth with good resistance to shriveling.
- *Color.*—Moderate Reddish-Brown (7.5R 3/6).

Flesh:
- *Color.*—Vivid Yellow (2.5Y 8/12) to moderate Reddish-Brown (7.5R 3/6).
- *Juice.*—Abundant.
- *Texture.*—Firm, melting when ripe.
- *Fibers.*—Few and fine.
- *Ripens.*—Generally even.
- *Eating quality.*—Good.

Stone: Tendency to cling.
- *Fibers.*—Few.
- *Size.*—Generally small.
- *Form.*—Generally oval.
- *Base.*—Usually straight to slightly oblique.
- *Hilum.*—Oval to round.
- *Sides.*—Usually equal.
- *Surface.*—Irregularly furrowed.
- *Color.*—Light brown.
- *Splitting tendency.*—None.

Use: Fresh market, local and distant.
- *Keeping quality.*—Good.
- *Shipping quality.*—Excellent.

Although the new variety of plum tree possesses the described characteristics of the growing conditions in Stanislaus County, California, having first been observed in Fresno County, California, in the central portion of the San Joaquin Valley, it is to be understood that variations of the usual magnitude in characteristics incident to the growing conditions, fertilization, pruning and pest control are to be expected.

Feb. 14, 1967 N. M. DARROW ETAL Plant Pat. 2,714
MANDARIN ORANGE PLANT
Filed Oct. 18, 1965
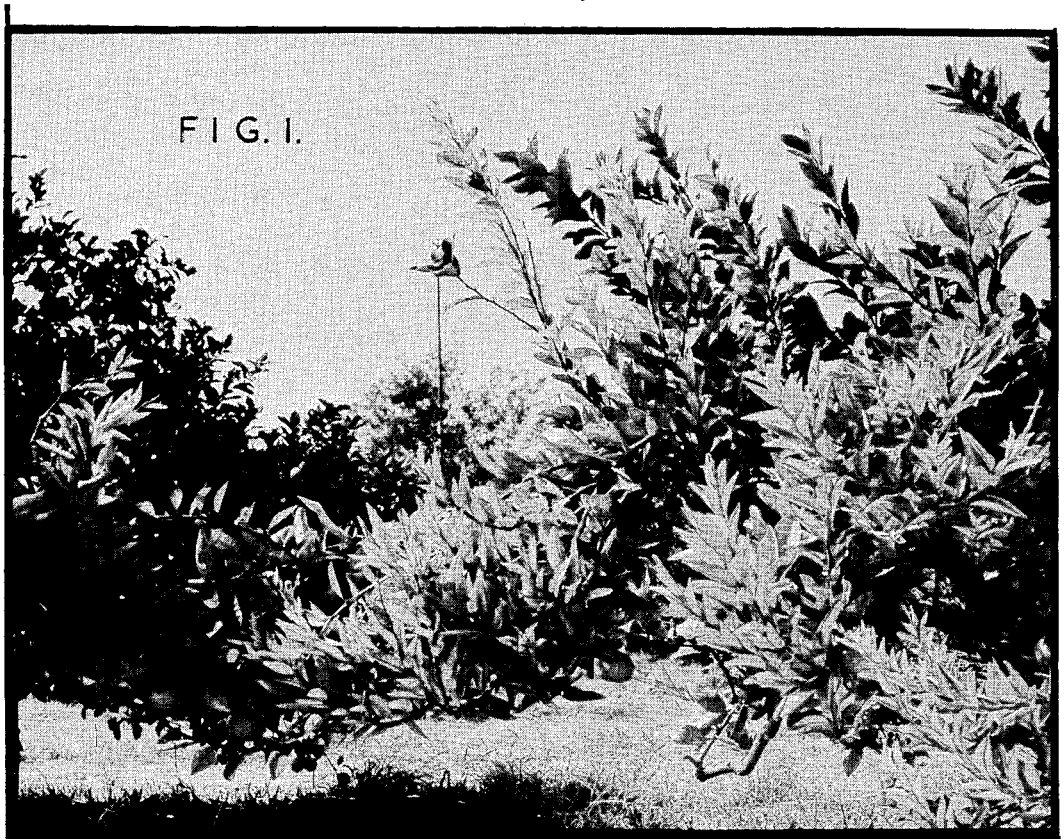
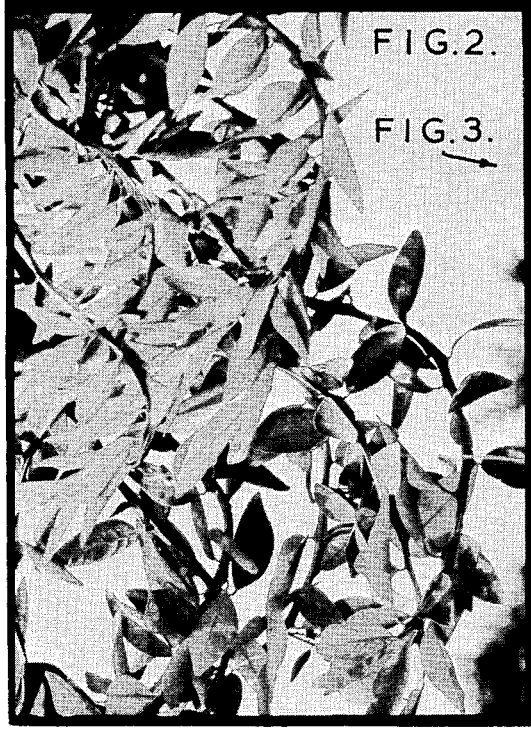
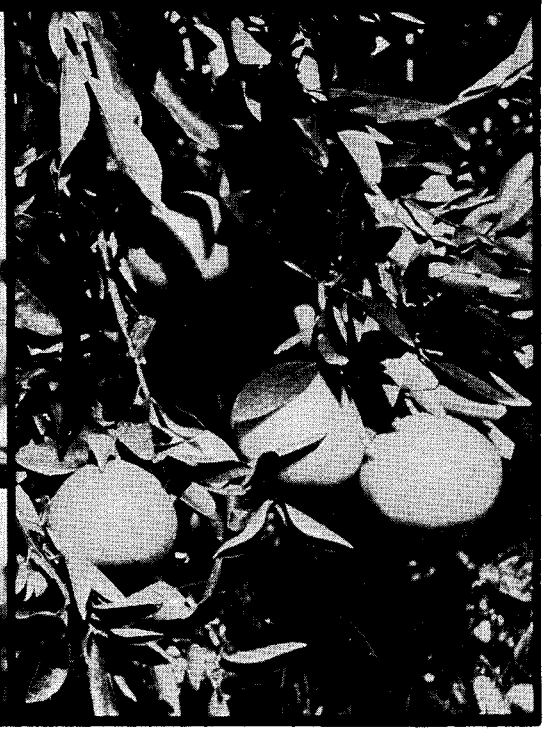
INVENTORS
Nance Marion Darrow and
Robin James Darrow
By Sparrow and Sparrow
ATTORNEYS